United States Patent
Hall et al.

(10) Patent No.: US 8,477,293 B2
(45) Date of Patent: Jul. 2, 2013

(54) METHOD AND APPARATUS FOR RAPIDLY COOLING A GEM, INCLUDING TWO STAGE COOLING

(75) Inventors: Matt Hall, West Chester, PA (US); Ren Lu, White Plains, NY (US); Wuyi Wang, Edison, NJ (US)

(73) Assignee: Gemological Institute of America (GIA), Carlsbad, CA (US)

( * ) Notice: Subject to any disclaimer, the term of this patent is extended or adjusted under 35 U.S.C. 154(b) by 738 days.

(21) Appl. No.: 12/380,445

(22) Filed: Feb. 27, 2009

(65) Prior Publication Data

US 2010/0220311 A1 Sep. 2, 2010

(51) Int. Cl.
*G01N 21/00* (2006.01)
(52) U.S. Cl.
USPC .......................................... 356/30; 250/341.1
(58) Field of Classification Search
USPC ................ 356/30; 250/341.1–341.2; 165/185
See application file for complete search history.

(56) References Cited

U.S. PATENT DOCUMENTS

| 4,284,894 | A  | * | 8/1981 | Sitte et al. ................... 250/443.1 |
| 4,802,343 | A  | * | 2/1989 | Rudick et al. ................... 62/294 |
| 7,324,188 | B1 | * | 1/2008 | Beesley ......................... 356/30 |
| 2006/0007656 | A1 | * | 1/2006 | Symons ........................ 361/699 |

* cited by examiner

*Primary Examiner* — Tri T Ton
(74) *Attorney, Agent, or Firm* — DLA Piper LLP (US)

(57) ABSTRACT

A cooling apparatus includes a container configured to contain a coolant within a space. The apparatus further includes a cooling block positioned substantially within the space and having a high heat capacity such that the space not occupied by the cooling block is filled with a coolant to a level at or below the top of the cooling block, and a placement structure having high thermal conductivity positioned on top of the cooling block and outside of the space. A method for cooling an object is also provided, which includes inserting a coolant into a container configured to contain the coolant within a space, and placing the object on a placement structure outside the space. For this method, the placement structure has a high thermal conductivity and is coupled to a cooling block, the cooling block having a high heat capacity and positioned substantially within the space. A two-stage cooling apparatus and method is also described.

12 Claims, 15 Drawing Sheets

US 8,477,293 B2

METHOD AND APPARATUS FOR RAPIDLY COOLING A GEM, INCLUDING TWO STAGE COOLING

TECHNICAL FIELD

The present invention is directed generally towards cooling an object, and more specifically towards a method and apparatus for rapidly cooling a gem so as to facilitate spectral analysis.

BACKGROUND OF THE TECHNOLOGY

It is often desirable to analyze properties of an object that has been cooled to very low temperatures, such as cryogenic temperatures, for example temperatures close to that of liquid nitrogen. When analyzing a gem, for example, it is often desirable to perform a spectral analysis of the gem at cryogenic temperatures to obtain information about the composition of the gem. Performing a spectral analysis on a gem cooled to such temperatures is particularly useful, for example, in determining the color origin of diamonds which may have been subjected to various treatments such as irradiation, as in a nuclear reactor or by an electron beam, or annealing, and for identifying diamonds treated under high-pressure and high-temperature (HPHT).

Currently available cooling apparatuses exhibit a number of disadvantages. For example, some currently available cooling apparatuses require a test sample to be cooled for approximately 20-30 minutes before a spectral analysis could be performed. Such a prolonged cooling period severely limits production capacity when a large number of gems need to be analyzed. Other apparatus employ direct immersion of the gemstone in the cooling medium which may result in undesirable interaction between the cooling medium and spectral information of interest. Still other cooling arrangements have employed a cylindrical copper block of approximately 2 inches in diameter, 1.8 inches in height, and having a 0.16 inch diameter bore along its axis, and which has been cooled to a desired temperature and removed from the cooling environment prior to placement of the object to be cooled in the 0.16 inch diameter bore.

Another disadvantage of some of the currently available cooling apparatuses is that they are bulky and complex. Some of these apparatuses, for example, require the test sample to be placed within a shell that is submerged in liquid nitrogen. Because of condensation that may occur within the shell, however, such apparatuses require a mechanism to infuse moisture-free gas into the enclosed internal chamber occupied by the test sample. As such, in addition to the extra time required to infuse gas into the shell, these apparatuses add additional costs to the analysis task, and because of their complexity are more prone to mechanical failure.

Accordingly, there is a need for a method and apparatus for rapidly cooling gems in an efficient and cost effective manner. More specifically, there is a need for a method and apparatus for cooling gems which does not require a closed environment, or infusion of moisture-free gas, and which allows for a rapid cool down and analysis of a large number of gems.

SUMMARY OF THE INVENTION

The present invention addresses the aforementioned problems by providing an improved method and apparatus for rapidly cooling gems in connection with analyzing the gems.

An embodiment of the present invention provides a cooling apparatus which includes a container having walls, such that the container is configured to contain a coolant within a space enclosed by the walls. The apparatus further includes a cooling block positioned substantially within the space and having a high heat capacity. The portion of the space not occupied by the cooling block is filled with a coolant to a level at or below the top of the cooling block. Such an embodiment also includes a placement structure having a high thermal conductivity positioned on top of the cooling block and outside of the coolant-filled space.

In another embodiment a cooling apparatus is provided including a container having an open end and a cooling block positioned within the container. For this embodiment, the cooling block has a high heat capacity, and a space between the cooling block and walls of the cooling apparatus is filled with a coolant to a level at or below the top of the cooling block. A placement structure having a high thermal conductivity is also provided, which is positioned outside of the coolant-filled space and in contact with a face of the cooling block that is accessible at the open end of the container.

In another embodiment of the present invention, a method for cooling an object is also provided, which includes inserting a coolant into a container configured to contain the coolant within a space and placing the object on a placement structure outside the space. Within such embodiment, the placement structure has a high thermal conductivity and is coupled to a cooling block. Also within this embodiment, the cooling block has a high heat capacity and is positioned substantially within the space.

In a further embodiment, a cooling apparatus is provided which includes a container configured to contain a coolant within a space. Within such embodiment, a cooling block having a high heat capacity is positioned substantially within the space such that the space not occupied by the cooling block is filled with a coolant to a level at or below the top of the cooling block. The apparatus also includes a placement structure having a high thermal conductivity, such that the placement structure is coupled to the cooling block and isolated from the space.

In another embodiment of the present invention, a method for cooling an object is provided, which includes pouring a coolant into a space bounded by a container and positioning the object on a placement structure having a high thermal conductivity. Within such embodiment, the placement structure is coupled to a cooling block having a high heat capacity and positioned substantially within the space, such that the object is isolated from the space.

In a further embodiment of the present invention, a two stage cooling apparatus is provided for cooling an object to be inspected. The apparatus comprises an outer container having walls, wherein the outer container is configured to contain a coolant within a space enclosed by the outer container walls; an inner container having walls, wherein the inner container is configured to contain a coolant within a space enclosed by the inner container walls and shaped to support the object to be inspected, and further wherein the inner container is supported in the outer container; and a coolant positioned in the outer container to a first level to partially fill the space enclosed by the outer container walls, and positioned in the inner container to a second level to partially fill the space enclosed by the inner container, wherein the first level is below an opening defined by the inner container walls. Preferably, the walls of the inner container define a hemispherical space and have a circular perimeter. The inner container may preferably comprise TEFLON® or SPECTRALON®, Aluminum, or Indium, depending upon its applications.

A still further embodiment of the present invention provides a two stage cooling of a gemstone and comprises a first coolant container; a second coolant container positioned within the first coolant container. The first coolant container includes walls formed of a thermally insulating material and an interior space which is capable of containing a first quantity of liquid phase coolant. The second coolant container includes an interior surface that is light reflective and with a "white" background or free of luminescence and capable of containing a second quantity of the liquid phase coolant. A first stage of cooling is provided to a gemstone positioned in the second coolant container when the first quantity of liquid phase coolant placed in the first coolant container, and a second stage of cooling is provided to the gemstone when the second quantity of liquid phase coolant placed in the second coolant container.

In another embodiment of the present invention, a two stage cooling process is implemented for cooling a gemstone for spectral analysis. The method comprises supporting the gemstone in an inner container constructed to light reflective and with a "white" background or free of luminescence, wherein the container is positioned within an outer container constructed of a thermally insulating material; providing a first stage of cooling to the gemstone by filling the outer container with liquid phase coolant to a level below a top opening of the inner container; and providing a second stage of cooling to the gemstone by filling the inner container with a coolant material to a level at which the gemstone is fully immersed in the coolant material and which is below the top opening of the inner container. Preferably, the inner container comprises TEFLON® or SPECTRALON® for a reflective "white" background, and aluminum or indium for free of luminescence.

In a further embodiment of the present invention, a two-stage cooling apparatus is employed with a multiple-channel, multiple-spectrometer arrangement, along with an optical probe that can be positioned in close proximity to a gemstone or other object to be inspected. With such an arrangement, improved signal to noise ratio and improved spectral resolution are achieved, in a rapid and accurate manner.

In yet another embodiment of the present invention, a system for evaluating a gemstone includes a two-stage cooling structure, including an outer coolant container constructed of thermally insulating material and an inner coolant container supported in the outer coolant container and constructed to be thermally conductive; a light source; a plurality of spectrometers, each selected to operate upon one of a plurality of different wavelength ranges; an optical probe and optical fiber assembly including a probe head, a plurality of optical fibers extending from the probe head as a bundle and then segregated into a plurality of sub-bundles; where at least one of the sub-bundles of fibers is configured to be coupled to the light source to provide a light path to the probe head; and others of the sub-bundles comprise selective absorption fibers, and further each such sub-bundles of fibers is selected to be responsive to a different predetermined range of wavelengths and are each configured to be coupled to a corresponding one of the plurality of spectrometers; and also, the optical probe is supported so that at least the probe head can be positioned in the inner coolant container.

In the foregoing embodiment, the plurality of spectrometers and the subgroups of selective absorption fibers may be selected to operate upon a plurality of overlapping ranges from approximately 190 nm to approximately 1050 nm.

Further, in the foregoing embodiment, a slit is selected to ensure the spectral resolution of selectively absorbed light that travels along the selective absorption fibers.

An object of the present invention is to provide improved cooling apparatus for rapidly cooling an object to be inspected, such as a gemstone.

A further object of the present invention is to provide a cooling apparatus that employs a coolant container having walls that extend to a selected height and are configured to contain a liquid coolant, and a cooling block having a high heat capacity and positioned within the coolant container, so that a top surface of the cooling block is positioned below the walls of the coolant container, such that when an object to be inspected is positioned on the top surface of the cooling block, and the cooling container is filled to a predetermined level with the liquid coolant, the object to be inspected is surrounded by a gaseous phase of the liquid coolant.

Another object of the present invention is to provide a two stage cooling apparatus for cooling a gemstone for spectral analysis.

A still further object of the present invention is to provide a two stage cooling apparatus for cooling a gemstone in which a first stage of cooling is provided by a first container filled with a first quantity of liquid phase coolant, and a second stage of cooling is provided by a second container positioned within the first container and filled with a second quantity of liquid phase coolant; wherein the first container is thermally insulating and the second container is light reflective and with a "white" background or free of luminescence.

It is a further object of the present invention to provide a system and method for evaluating a colored gem stone which has been cooled to below a designated temperature using a two stage cooling arrangement.

It is a still further object of the present invention to provide a system and method for evaluating a colored gem stone which has been cooled to below a designated temperature using a two stage cooling arrangement and a multiple-channel, multiple-spectrometer arrangement.

Through the use of a device and method in accordance with the present invention spectral patterns have been obtained which much more accurately reflect the color of analyzed samples.

As will be appreciated upon consideration of the following detailed description of the invention and accompanying drawings, there are many advantages and features of the present invention, which in turn lead to many new and useful applications of the invention.

DETAILED DESCRIPTION OF THE INVENTION

The present invention is directed towards providing an improved method and apparatus for cooling objects by the use of a coolant. In a particular application, the present invention provides an efficient open to the air solution for rapid cooling of gems to cryogenic temperatures, for use in a system that perform spectral analysis of gems at such temperatures. Moreover, for such applications, a significant improvement from prior art methods and apparatuses is provided since the present invention cools gems much faster and does not require complex mechanisms that infuse moisture-free gas. Such an improvement is particularly useful when a large number of gems need to be individually analyzed.

Figure 1:
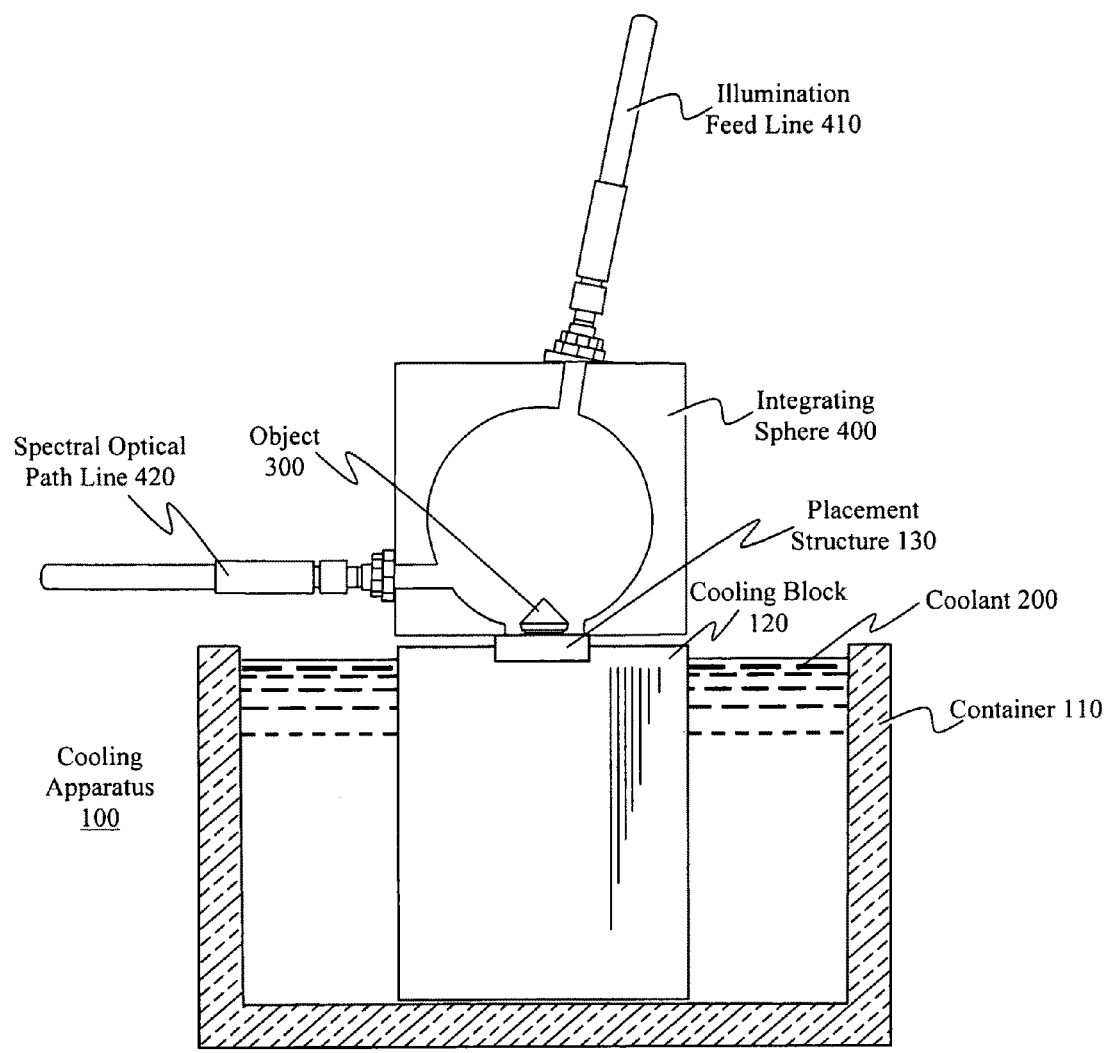
FIG. 1 is an exemplary cooling apparatus having low walls according to an embodiment of the invention.

In FIG. 1, an exemplary cooling apparatus according to an embodiment of the invention is provided. As illustrated, a cooling apparatus 100 includes a container 110, a cooling block 120, and a placement structure 130. In a preferred embodiment, placement structure 130 is positioned on top of cooling block 120, and cooling block 120 is positioned in the center of container 110, as shown.

In use, cooling apparatus 100 may be used in conjunction with an integrating sphere 400 to analyze the spectral properties of an object 300 cooled to a desired temperature. Within such embodiment, the space between cooling block 120 and container 110 is preferably filled with a coolant 200 (e.g., liquid nitrogen) to a height just below the top of cooling block 120, as shown. By selecting a cooling block 120 with a sufficiently high heat capacity, and by selecting a placement structure 130 with a sufficiently high thermal conductivity, object 300 is quickly and effectively cooled to the desired temperature. Preferably, the sample is first cooled down to the coolant (e.g. liquid nitrogen) temperature quickly by direct immersion in coolant, then transferred to the block. In this way, the sample is cooled down even faster, and also properly maintained. Once object 300 is cooled, integrating sphere 400 may then be positioned over object 300 and about placement structure 130 as shown. Object 300 may then be illuminated via illumination feed line 410, and spectral response information may then be collected via spectral optical path line 420.

In the discussion that follows, the structural dimensions of various aspects of the present invention are discussed, and dimensions for a particular embodiment are given. However, it should be noted that such dimensions are provided solely as an example of particular embodiments and are not intended to limit the scope and spirit of the invention. Furthermore, it will be apparent to one skilled in the art upon reading these descriptions that other materials, dimensions, configurations and arrangements can be used to implement the teachings of this application and the concepts of the present invention.

As shown in FIG. 1, the illustrated embodiment includes an insulation container 110 preferably having a rectangular cross section. A variety of container shapes may be used, including cylindrical and cubic shaped containers. In a prototype of cooling apparatus 100, insulation container 110 was made of Styrofoam® material, in which the walls had a height of approximately 20 cm uniform thickness of approximately 5 mm and the dimensions of the base were approximately 20 cm. For the particular embodiment of FIG. 1, it should be appreciated that the side walls were configured to have a uniform height substantially even with the height of cooling block 120, as shown.

Meanwhile, cooling block 120 fits substantially within insulation container 110, as shown, where it firmly rests either due to its weight alone or from being affixed to the base of insulation container 110. In a preferred embodiment, cooling block 120 has a cylindrical shape and has a high heat capacity, which provides a "heat sink" so that object 300 is cooled to a temperature at or about the temperature of cooling block 120. Cooling block 120 is preferably made from a material and has a mass such that the heat energy required to increase the temperature of cooling block 120 by a certain temperature interval is large, so that the object 300 being evaluated quickly reaches a temperature at or near the temperature of cooling block 120. In a preferred use of the embodiments of the cooling apparatus, a sample is first pre-cooled in coolant located either external to or within the container 110, and then placed upon the cooling block 120, which permits a very low temperature to be maintained by the block. Materials which have high heat capacity suitable for use in the invention include, for example, copper, iron, indium. In a prototype, cooling block 120 was made of copper having a height of approximately 70 mm and a diameter of approximately 63.5 mm.

Figure 2A:
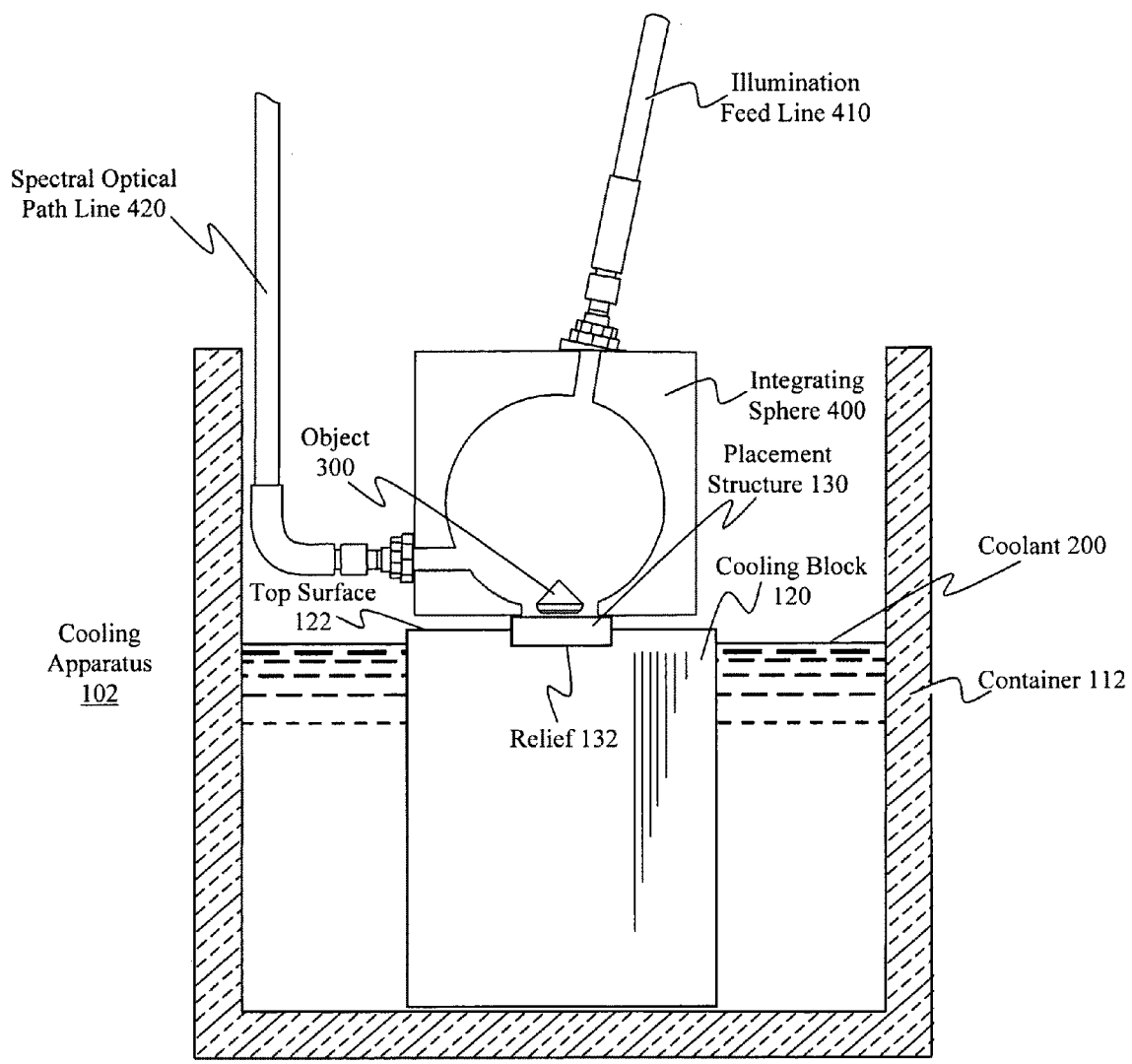
FIG. 2A is an exemplary cooling apparatus having high walls, wherein the spectral analysis optical path line is routed to enter the enclosed space through the open end of the container, according to an embodiment of the invention.
Figure 2B:
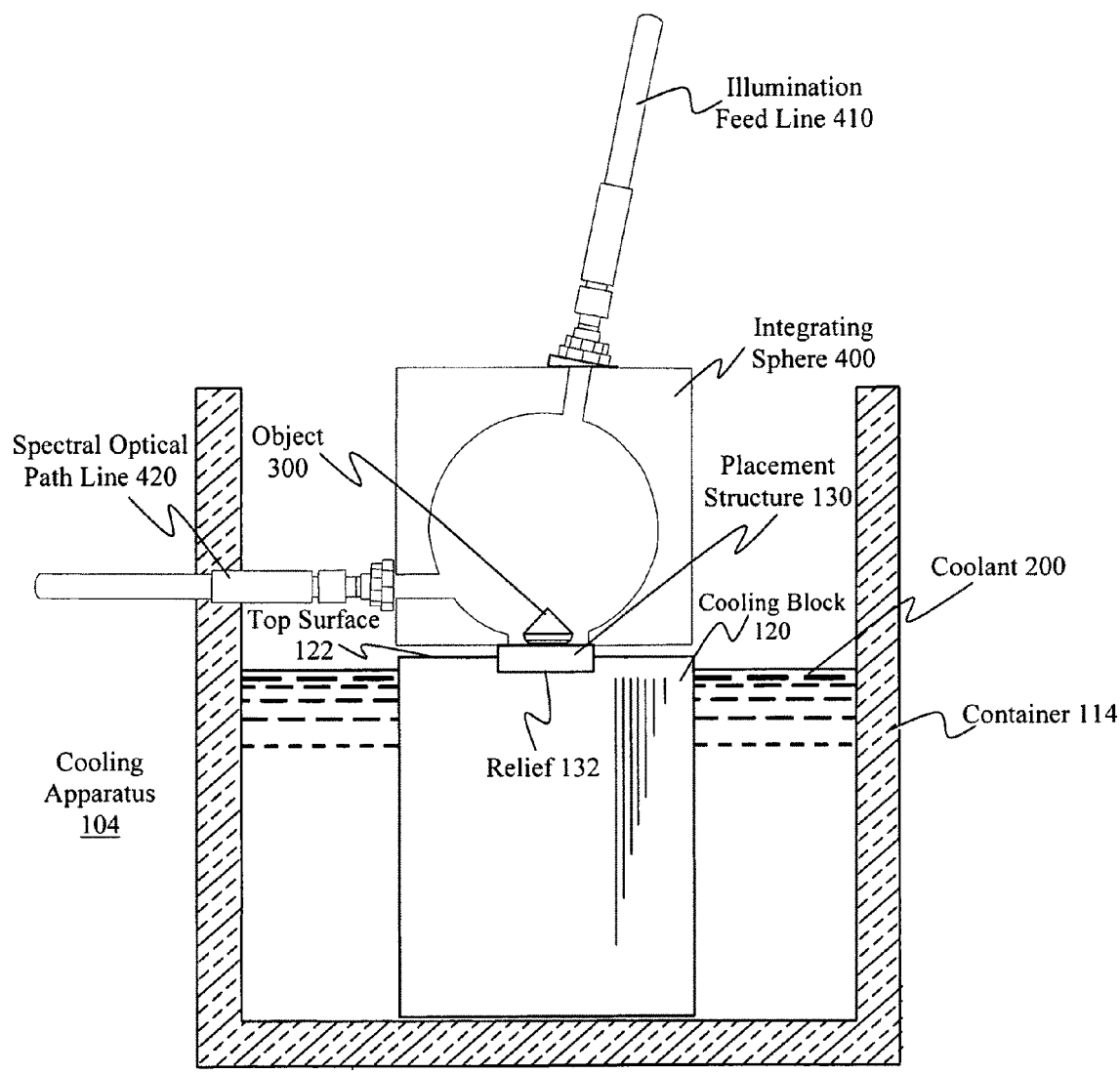
FIG. 2B is an exemplary cooling apparatus having high walls, wherein the spectral analysis optical path line is routed through a very narrow slit in the high walls that is dimensioned to accommodate an optical fiber, according to another embodiment of the invention.

Placement structure 130 is preferably positioned on top surface 122 of cooling block 120, as shown for example in FIGS. 2A and 2B, where it is preferably positioned within a relief 132 formed within the top surface 122. Placement structure 130 may be friction-fit into relief 132, affixed to top surface 122 by way of a suitable thermally conductive adhesive, or attached to stop surface 122 through other suitable mechanisms which promote thermal conduction between placement structure 130 and cooling block 120. In a preferred embodiment, placement structure 130 is disc-shaped and has a high thermal conductivity so as to facilitate an efficient transfer of energy from object 300 to cooling block 120. Preferably, materials having thermal conductivity at or above that of high purity alumina or SPECTRALON® polymer material may be used for placement structure 130. For some embodiments, the desired conductivity may be achieved by constructing placement structure 130 out of aluminum. For particular applications, however, it should be appreciated that placement structure 130 may need to exhibit properties not necessarily provided by aluminum. For spectral analysis, for example, a placement structure 130 that provides a background for object 300 that minimizes false readings, may be used. Also, the placement structure may be configured to promote coupling to integrating sphere 400. For such embodiments, placement structure 130 preferably utilizes materials with high thermal conductivity and which provide a "white" background, such as any of a plurality of materials including TEFLON®, white ceramic, boron silicate, and aluminum oxide. Placement structure 130 may be made entirely of such materials or such materials may be used to line the surface of placement structure 130. Placement structure 130 may thus be designed to provide both high thermal conductivity and a background having a desired absorption characteristics. In a preferred embodiment, placement structure 130 may be a disc of TEFLON® polymer material having a thickness of approximately 0.1 inch and a diameter of approximately 1.0 inch.

In a preferred embodiment, it should be appreciated that cooling apparatus 100 may be used for spectral analysis in conjunction with any of a plurality of commercially available integrating spheres 400. In a prototype, an integrating sphere 400 manufactured by Avantes BV, of Eerbeek, Netherlands, was used, which included an illumination feed line 410 and a spectral optical path line 420, as shown. During use, integrating sphere 400 is coupled to placement structure 130 so as to substantially cover object 300. Illumination feed line 410 provides light to the inner portion of integrating sphere 400 so as to provide illumination for object 300. Spectral optical path line 420 provides an optical path for communicating the resulting spectral response of object 300 to analysis equipment such as a spectrometer. The above arrangement facilitates spectral analysis of object 300 which has been cooled by cooling apparatus 100.

In a preferred embodiment of the invention, as illustrated in FIGS. 2A and 2B, the walls of container 112 (and container 114) are designed to extend to a height substantially higher than the height of cooling block 120, and thereby to extend to a height substantially higher than the top of object 300 when placed on placement structure 130, as shown. In a prototype, the walls were designed to extend approximately 2 inches higher than the height of object 300. By implementing such a design, when coolant 200 is in liquid form, such as dry liquid nitrogen, vaporized gas emanating from coolant 200 will fill the space above coolant 200 and displace the ambient gases from around object 300. The vaporized gas from coolant 200 may flow over the heightened walls of containers 112 or 114, for example, thus filling the interior space above cooling block 120 and coolant 200 with the vaporized gas. As a result, the vaporized gas is present above the top of cooling block 120 and serves as a dry atmosphere to prevent condensation on object 300.

When such an embodiment is used in conjunction with integrating sphere 400, it should be further noted that spectral optical path line 420 may either be routed along the interior and over the top of the walls of container 112, as shown in FIG. 2A, or through a wall of container 114, as shown in FIG. 2B. Preferably, for the configuration of FIG. 2B, a narrow slit, of about 5 mm in width, is provided for passage of the fiber through the container wall.

Figure 3A:
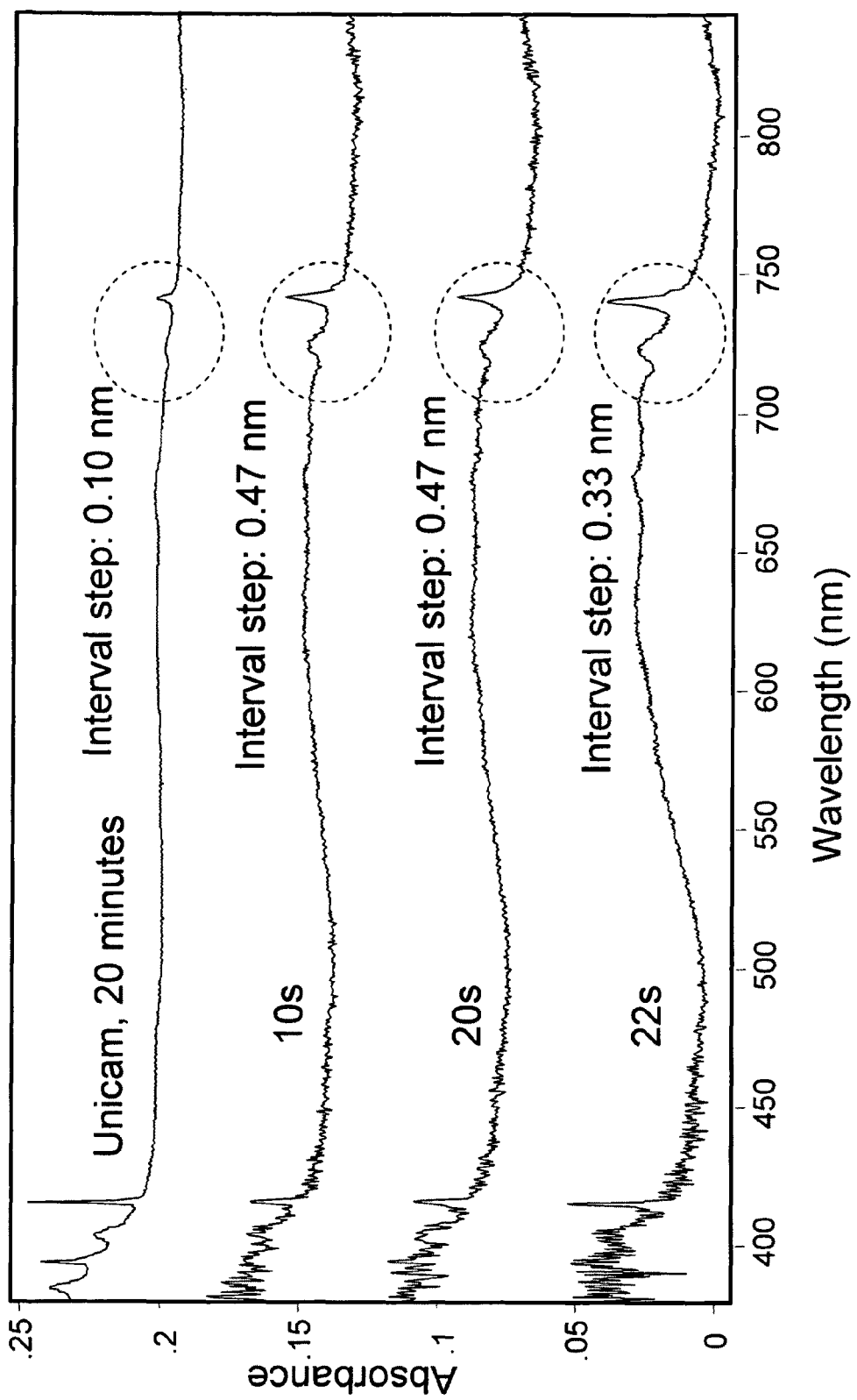
FIG. 3A is an exemplary graph comparing the spectral analysis of a 0.16 carat gem obtained using an apparatus of the prior art versus an apparatus according to an embodiment of the invention.
Figure 3B:
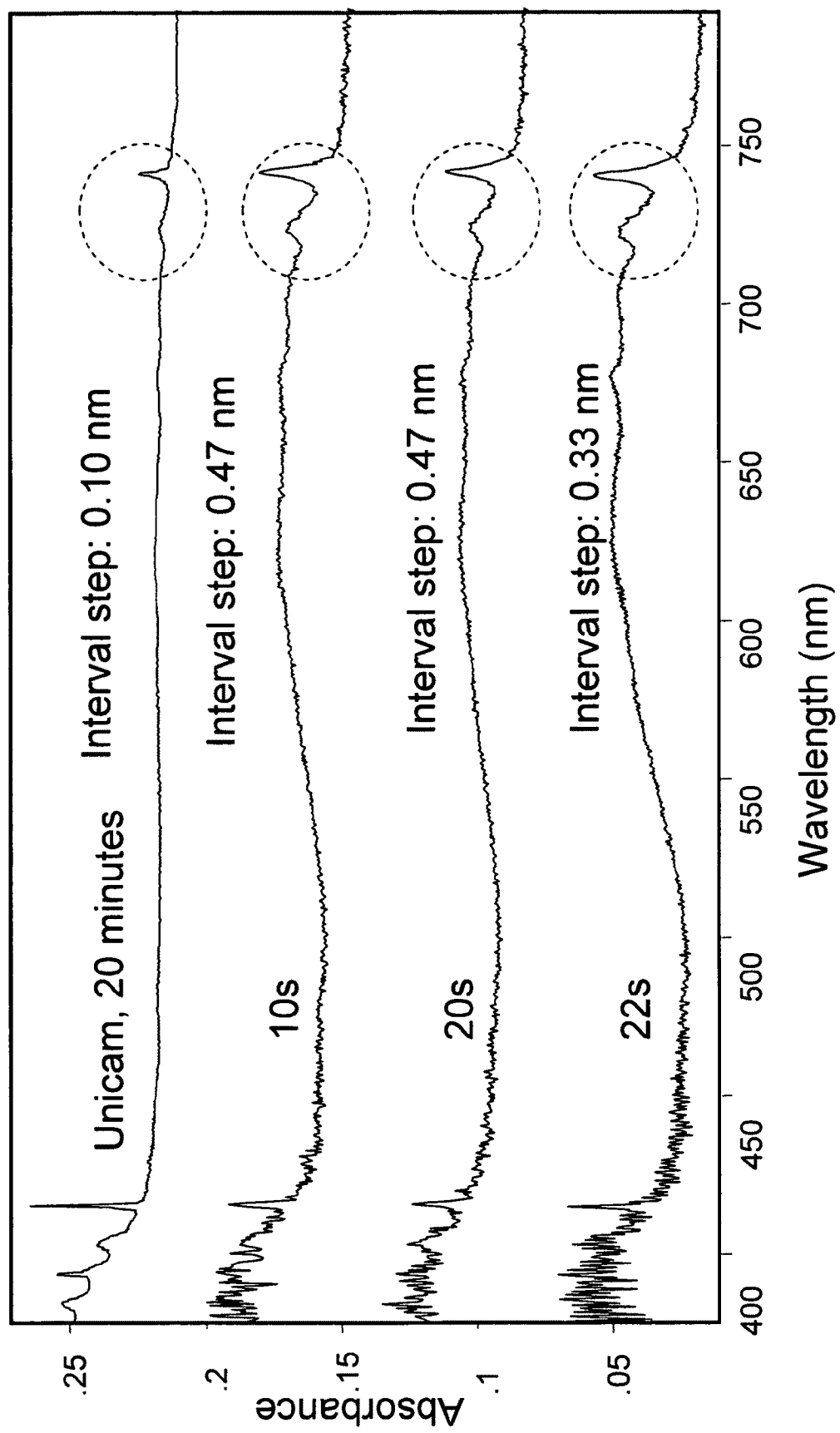
FIG. 3B is an exemplary graph comparing the spectral analysis of a 0.11 carat gem obtained using an apparatus of the prior art versus an apparatus according to an embodiment of the invention.
Figure 3C:
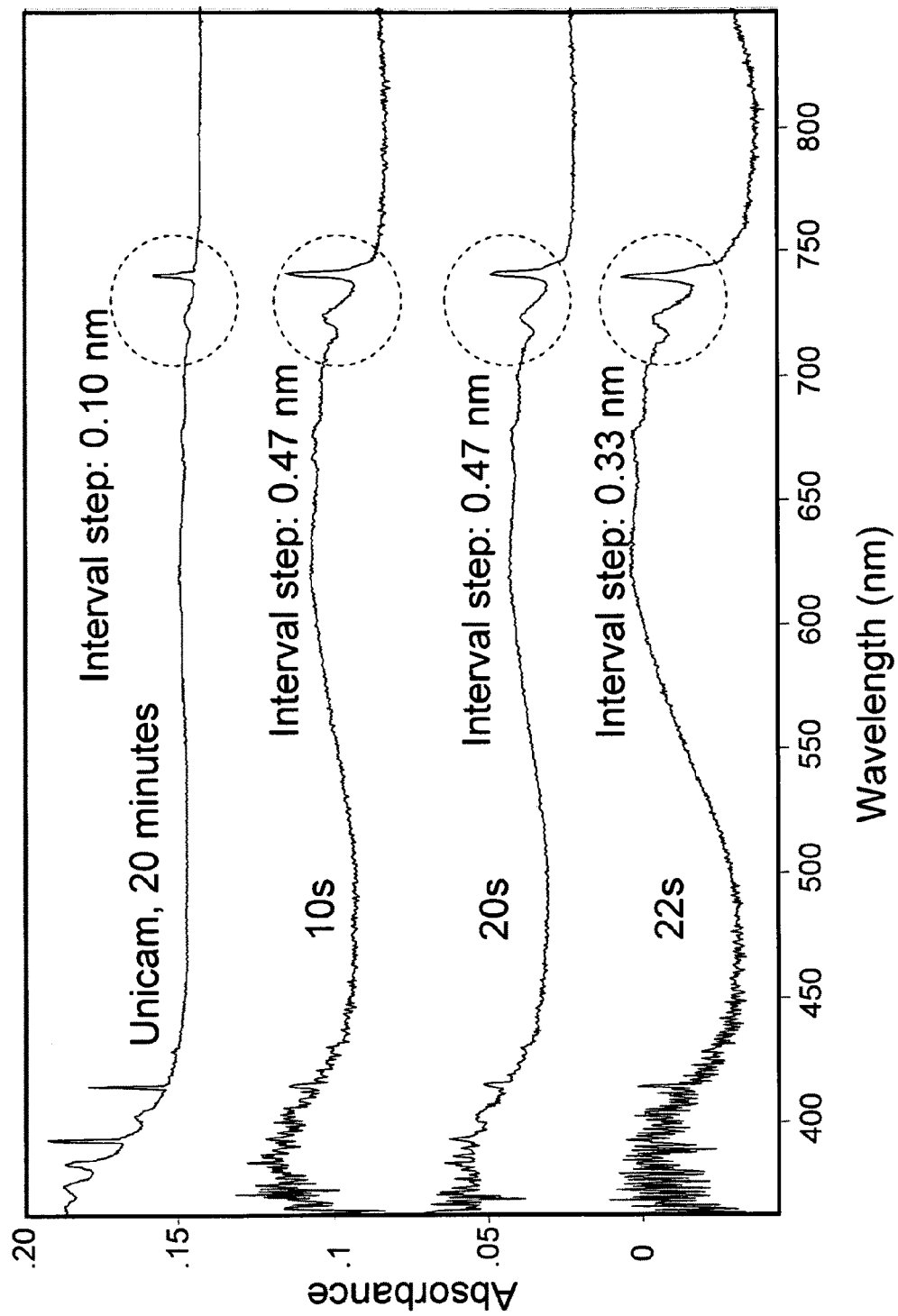
FIG. 3C is an exemplary graph comparing the spectral analysis of a 0.14 carat gem obtained using an apparatus of the prior art versus an apparatus according to an embodiment of the invention.

The present invention has provided a useful tool for performing spectral analysis on gems, which require the gems to be cooled to a particular temperature. Namely, relative to prior art apparatuses, the present invention provides a cooling apparatus which cools gems much faster and yields spectrums of much higher quality. To better illustrate the utility of the present invention, FIGS. 3A-3C provide charts illustrating a comparison of plots of spectral responses of gems weighing 0.16, 0.11, and 0.14 carats obtained using an apparatus of the prior art versus an apparatus according to an embodiment of the invention. In each of these charts, four plots are provided. One plot shows the spectrum obtained, plotted at an interval step of 0.10 nanometers, using a prior art apparatus in which the gem had been cooled for approximately twenty minutes. Using the prior apparatus, it takes about 20 minutes to get the sample cooled down and about another 20 minutes to collect a spectrum. The prior art apparatus employed a Unicam spectrometer with cryostat, provided by Thermo Elemental, of Franklin, Mass. The other three plots were obtained using embodiments of the present invention for spectral accumulation of the gem at each of ten, twenty, and twenty-two seconds, and plotted at interval steps of 0.47, 0.47, and 0.33 nanometers, respectively. A system by which the spectral information was analyzed and plotted to yield these plots is described in further detail in co-pending U.S. patent application Ser. No. 12/380,425, entitled "FAST UV-VIS-NIR ABSORPTION SPECTROMETER SYSTEM AND METHOD", filed even-date herewith, and incorporated by reference herein in its entirety ("Gem Spectral Analysis System Application"). As illustrated, in addition to cooling the gems much more quickly than the prior art apparatus, the present invention provides a relatively higher quality spectrum that includes less noise for a wavelength region between 450 and 850 nanometers. In FIGS. 3A-3C, for example, the plotted response in the wavelength region between 700 and 750 nanometers has been circled to highlight the higher quality of the spectrums obtained, over a substantially shorter amount of time, using the present invention compared to that obtained though the prior art arrangement.

Figure 3D:
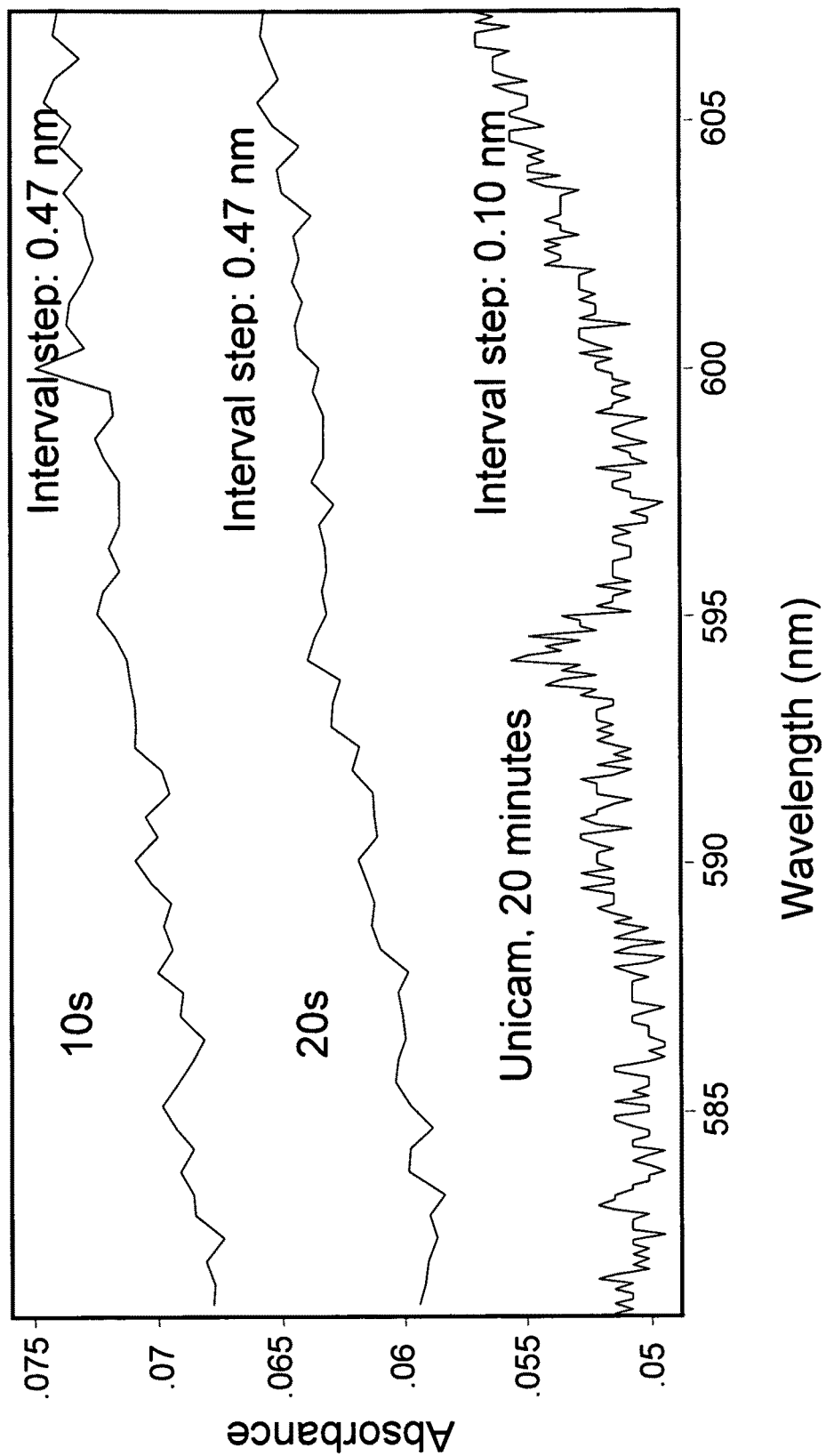
FIG. 3D is an exemplary graph comparing an enlargement of a portion of the spectral analysis of a 0.10 carat gem of FIG. 3C obtained using an apparatus of the prior art versus an apparatus according to an embodiment of the invention.

In FIG. 3D, an exemplary graph comparing the spectral response, over a 580 nm to 610 nm range, of a 0.10 carat gem obtained using an apparatus of the prior art versus an apparatus according to an embodiment of the invention is provided. For this particular graph, spectrum responses plotted at interval steps of 0.47 nanometers of the gem cooled by the present invention for each with spectral accumulation time of ten and twenty seconds are compared to a spectrum taken at an interval step of 0.10 nanometers of the same gem cooled by a prior art apparatus, which required a cooling time of approximately twenty minutes and another twenty minutes for spectral acquisition. As illustrated, FIG. 3D shows how quickly the spectrum obtained using the present invention "sharpens up" relative to the spectrum obtained by the prior art apparatus. FIG. 3D thus illustrates how rapidly spectral information can be obtained with reduced noise characteristics.

Figure 3E:
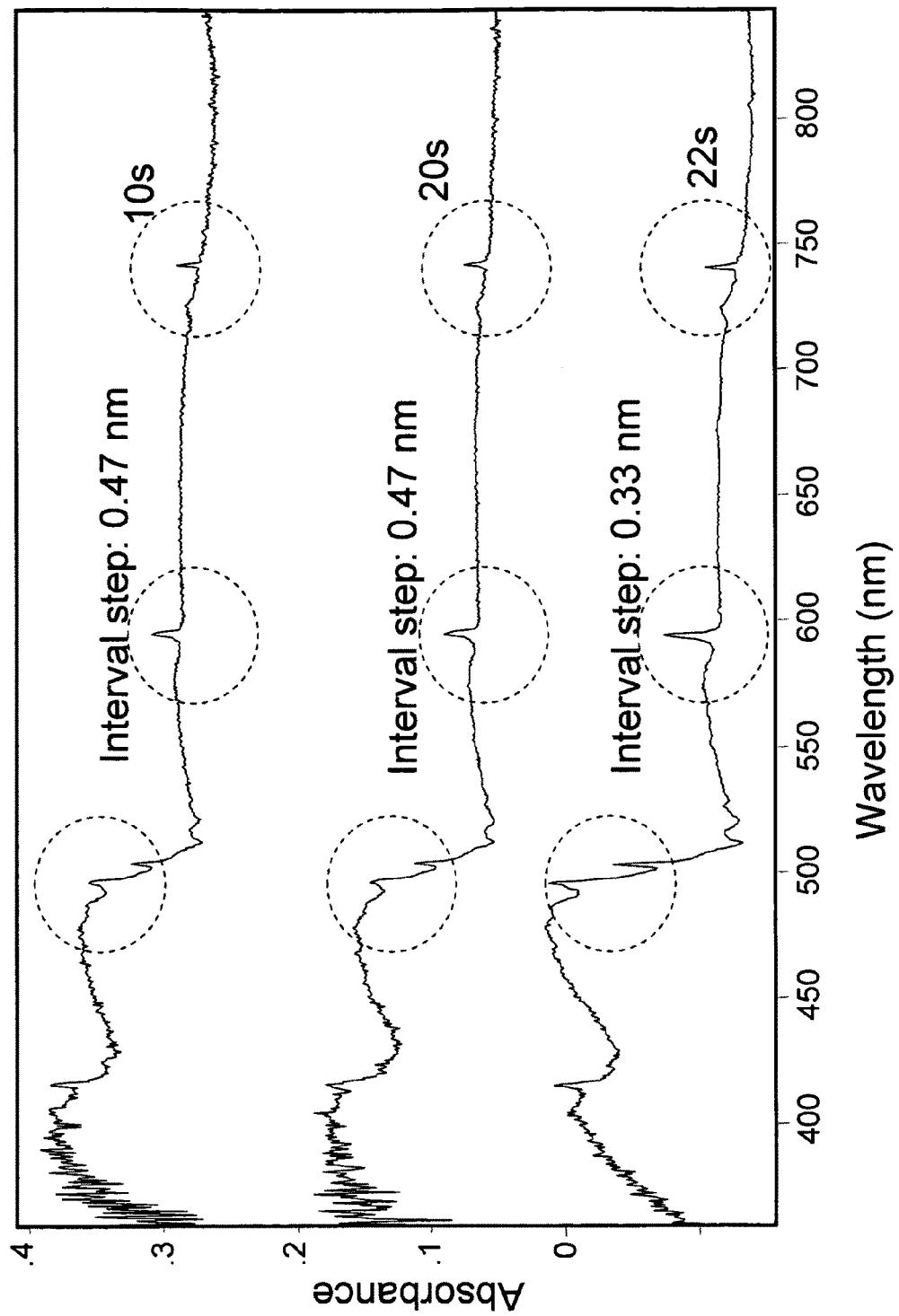
FIG. 3E is an exemplary graph comparing the spectral analysis of a 0.50 carat gem obtained at different cooling times using an apparatus according to an embodiment of the invention.

In FIG. 3E, an exemplary graph comparing the spectral analysis of a 0.50 carat gem obtained at different spectral accumulation times using an apparatus according to an embodiment of the invention is provided. In particular, three plots are provided which represent the spectra produced with accumulation time of ten, twenty, and twenty-two seconds, and at interval steps of 0.47, 0.47, and 0.33 nanometers, respectively. As illustrated, the spectrum produced with accumulation time of twenty-two seconds shows a relatively higher quality spectrum in terms of reduced noise than the spectrums produced with accumulation time of ten and twenty seconds. However, it is also to be noted that even after only 10 seconds of data accumulation, the spectrum peaks and general spectral characteristics are already apparent. In the wavelength region between 350-400 nanometers, for example, the plot representing the twenty-two second of data accumulation period exhibits much less noise than the plots representing the ten and twenty second accumulation periods. As illustrated, the peaks, while present in all of the plots, are also relatively more defined in the plot for the twenty-two second accumulation period compared to the plots for the ten and twenty second accumulation periods (see e.g., the peaks at approximately 503, 595, and 741 nanometers).

Figure 3F:
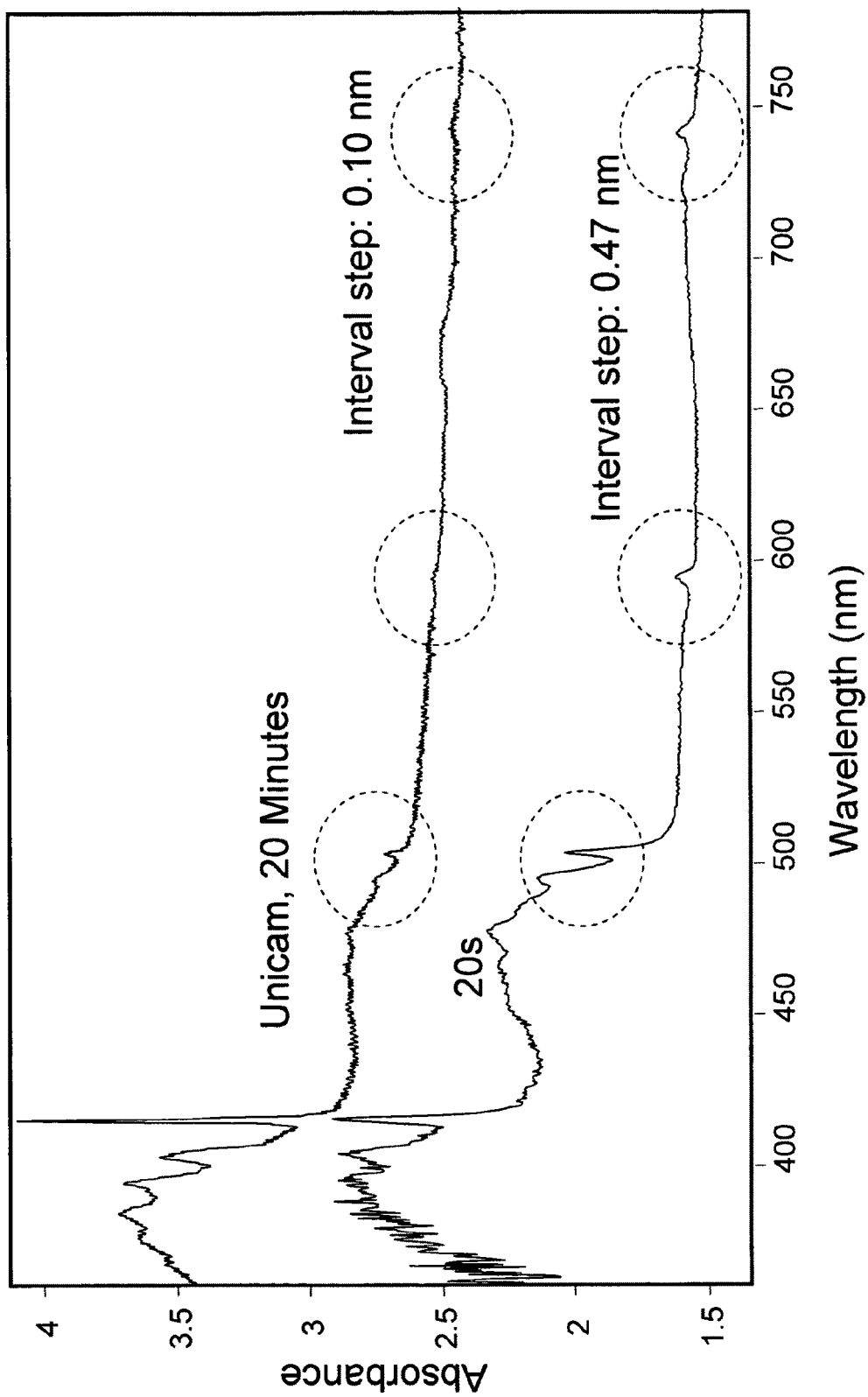
FIG. 3F is an exemplary graph comparing the spectral analysis of a 2.5 carat gem obtained using an apparatus of the prior art versus an apparatus according to an embodiment of the invention.

In FIG. 3F, an exemplary graph comparing the spectral response of a 2.5 carat gem obtained using an apparatus of the prior art versus an apparatus according to an embodiment of the invention is provided. For this particular graph, the spectrum (plotted at an interval step of 0.47 nanometers) for the gem collected by the present invention for twenty seconds, is compared to a spectrum (plotted at an interval step of 0.10 nanometers) of the same gem cooled by a prior art apparatus, which required a cooling time of approximately twenty minutes and data acquisition of another twenty minutes. As illustrated, not only are the plots relatively similar for the wavelength region below 450 nanometers, but the quality of the spectrum for wavelengths greater than 450 nanometers obtained using the present invention is markedly cleaner and higher sensitivity than the spectrum obtained using the prior art apparatus. Namely, through the use of the present invention a spectrum was obtained with much less noise, much more defined peaks, and substantially more quickly than that obtained using the prior art arrangement (see e.g., the peaks at approximately 503, 595, and 741 nanometers).

Figure 4:
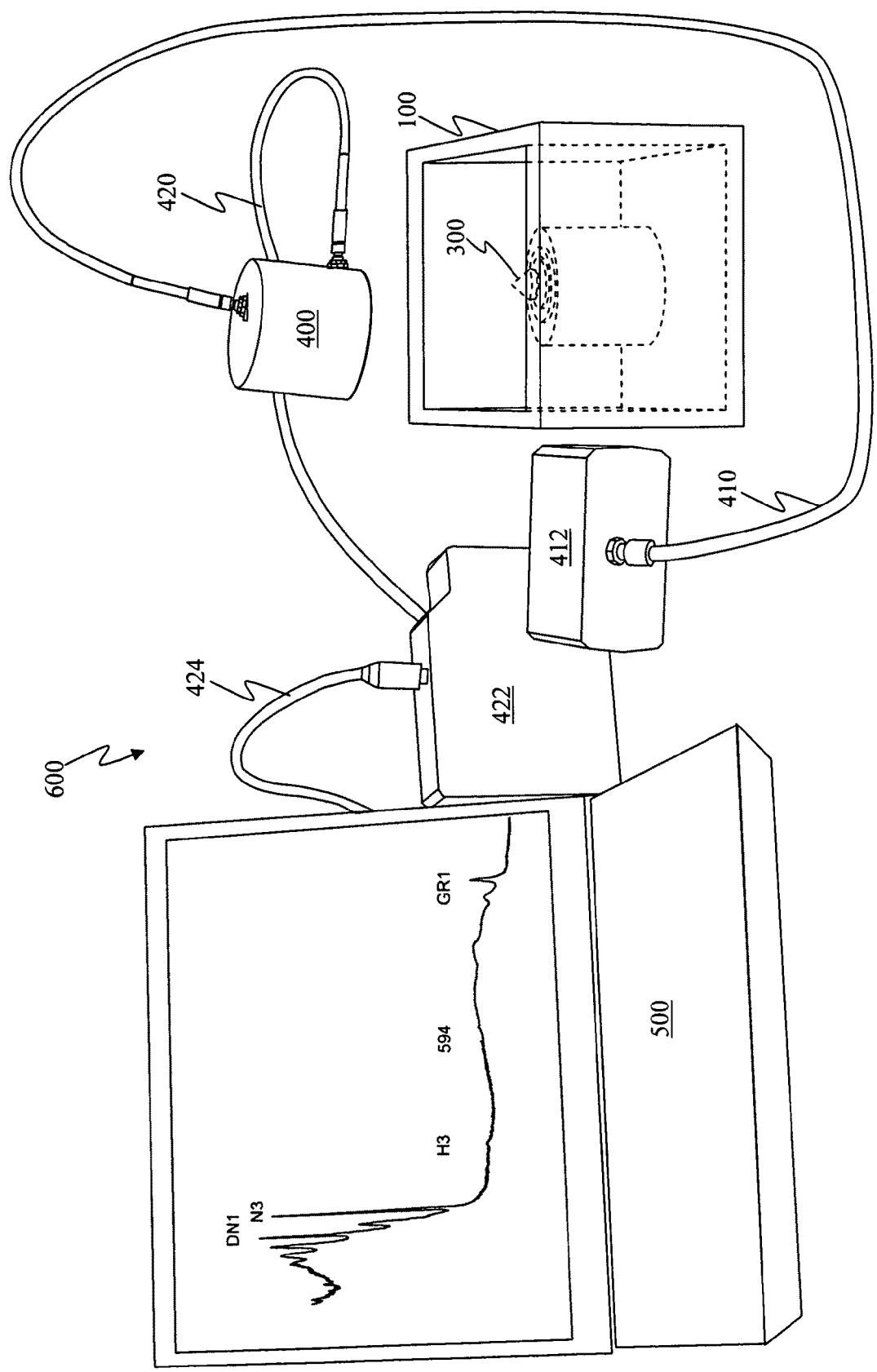
FIG. 4 is a schematic of a system employing an embodiment of a cooling apparatus according to an embodiment of the invention.

Referring to FIG. 4, the components of an embodiment of a gem spectral analysis system 600 which incorporates the cooling structure of the present invention will now be briefly described. Such a gem spectral analysis system may be that which is described in the "Gem Spectral Analysis System Application" referenced hereinabove.

In gem spectral analysis system 600, gem cooling apparatus 100 is provided for cooling an object 300 being evaluated to a desired temperature. An integrating sphere unit 400 is placed over an object 300. Object 300 is cooled to the desired temperature by cooling apparatus 100. Although reference is made to gem cooling apparatus 100, it is to be understood that the embodiments of gem cooling apparatus 102 and 104 may also be used in gem spectral analysis system 600.

Integrating sphere unit 400 illuminates the object 300 with electromagnetic radiation, which may be light of selected wavelengths, and then gathers the spectral response of the illuminated gem. Integrating sphere unit 400 may be implemented using model no. AvaSphere-50, manufactured by Avantes BV of Eerbeek, Netherlands. The selected wavelengths of light for illuminating object 300 may be provided by a light source 412, such as a tungsten halogen light source model AVALight-Hal-S, manufactured by Avantes BV of RB Eerbeek, Netherlands. Optical cable 410 may be used to route light from light source 412 to the integrating sphere unit 400. The gathered spectral response from integrating sphere unit 400 may be routed over optical cable 420 to a high resolution spectrometer unit 422, such as model no. HR4000, manufactured by Ocean Optics of Dunedin, Fla. The high resolution spectrometer unit 422 measures the amount of light as a function of wavelength in the gathered spectral response and transforms the measurements into digital information. The gathered spectral response data, in digital form, is then provided for further processing by computer 500. Cable 424 may be used to couple spectrometer unit 422 to computer 500 to provide a path for the spectral response data.

Computer 500 preferably includes software applications by which the spectral response information from spectrometer unit 422 may be further processed. Such processing may be for purposes of displaying an image on a computer screen of a depiction of the spectral response as a function of wavelength, as shown in FIG. 4, for detecting and analyzing characteristics of the spectral response, for extracting specified data from the spectral response information, and the like. Although a laptop computer is depicted in FIG. 4, it is to be understood that other computing or processing devices such as a desktop computer or dedicated controller unit, and the like, may be used, with or without an image display, within the spirit of the present invention.

Figure 5:
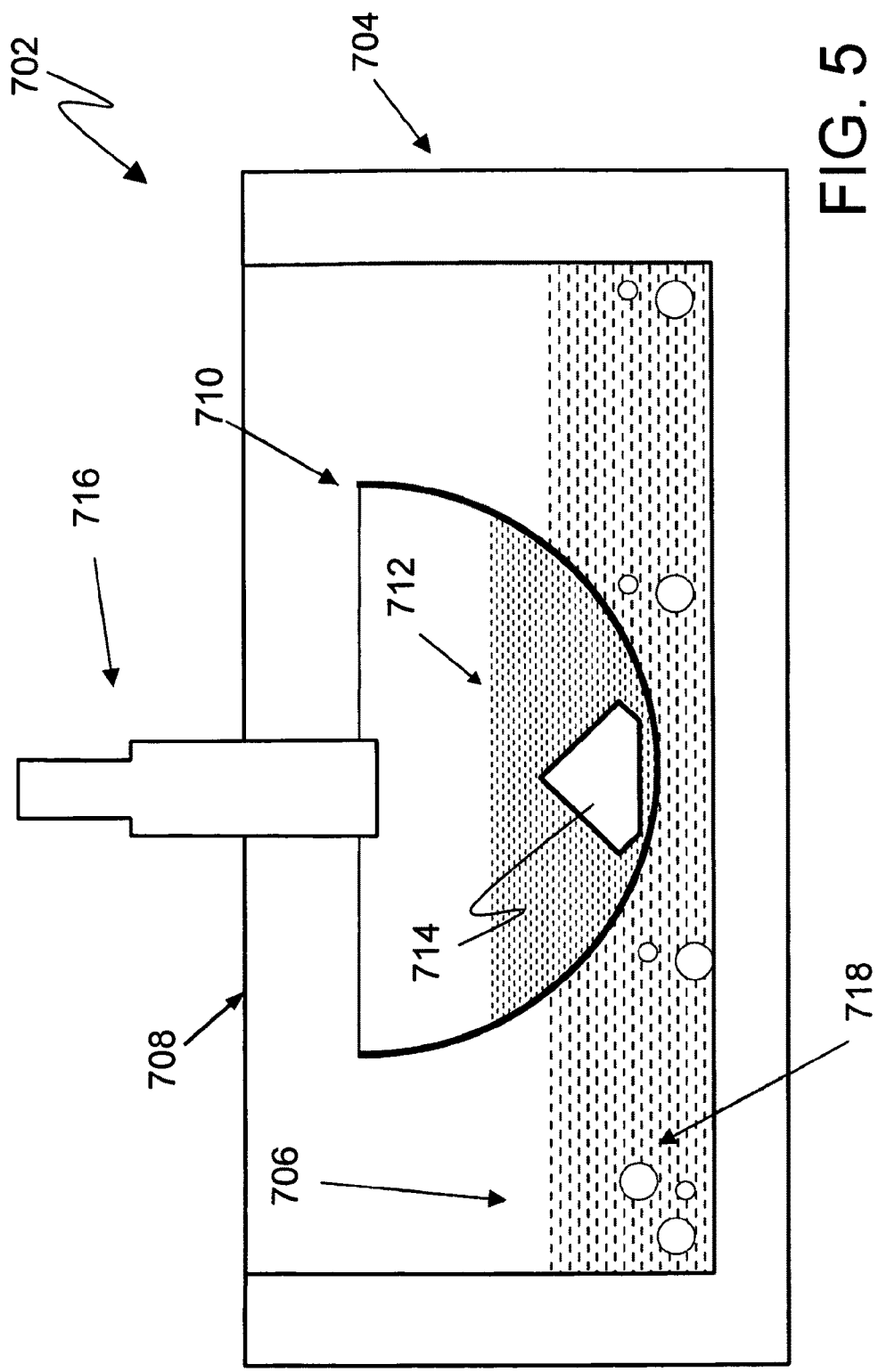
FIG. 5 is a simplified cross-sectional view according to a two-stage cooling embodiment of the invention illustrating the relative positioning of an inner coolant container, an outer coolant container, the gemstone to be inspected, an optical probe used for the inspection, and levels of liquid phase coolant.

Referring now to FIG. 5, a two-stage cooling embodiment 702 of the present invention will now be described. In accordance with the multi-stage cooling approach, a pair of liquid-phase coolant containing structures is used. A first, or outer, container 704 is preferably constructed of a thermally insulting material such as a foam. The outer container 704 is shaped so that it can accommodate a quantity of liquid phase coolant 706, preferably liquid nitrogen. Preferably, outer container 704 is open at the top, with its walls defining a perimeter 708. Outer container 704 may be constructed of Styrofoam® brand foam.

A second, or inner, container 710 is positioned and supported within the outer container 704. The inner container 710 is also shaped so to accommodate a quantity of liquid phase coolant 712, preferably liquid nitrogen. Inner container 710 is preferably constructed using materials with a "white" background or materials free of luminescence.

More specifically, it is desired that materials positioned with inner container 710 be cooled by coolant located in outer container 704, so as to provide a first stage of cooling. Thus, it is preferred that inner container 710 has a thermal conductivity that will permit such cooling. Therefore, when inner container 710 is filled with a liquid phase coolant, and an object 714, such as a gemstone, is immersed in the coolant, such coolant is itself cooled by the coolant in first container 704, and also provides a second stage of cooling to the object. Although not shown, it is to be understood that when probe 716 is positioned so that its probe head is located within inner container 710, the probe head will be surrounded by a gaseous phase of liquid-phase coolant 712.

The desired thermal conductivity can be achieved, for example by employing a thermally conductive material, or adjusting the thickness of the walls of the container, or both.

Further, it is desired that the interior surfaces of inner container 710 be light reflective and with a "white" background and has no significant selective absorption over the interested spectral region. It has been found that with such inner surface of inner container 710 being light reflective and suitably shaped, an optical probe 716 positioned above object 714 and so out of contact with liquid phase coolant 712 is able to gather a substantial and sufficient quantity of light from inner container 710 for spectral analysis purposes.

Preferably, inner container 710 has the shape of a hemisphere, or half-ball. The walls of inner container 710 preferably define a top opening having a perimeter that has a circular shape. A suitable light reflective inner surface can be obtained by constructing at least the inner surface out of TEFLON® or SPECTRALON®. Aluminum is another material suitable for the construction of inner container 710, and that provides satisfactory results, for both thermal conductivity, light reflectivity, and free of luminescence. With such a construction, it has been found that an integrating sphere, as was employed with the embodiments of FIGS. 1, 2A and 2B, is unnecessary.

In operation, and according to a method of the present invention, object 714 is placed in and supported by inner container 710. A quantity of liquid phase coolant 706, such as liquid nitrogen, is placed into outer container 704 so that the container 710 is sufficiently cooled down and separated from direct contacting with surrounding air. A quantity of liquid phase coolant 712, such as liquid nitrogen, is placed into inner container 710 so that object 714 is immersed in coolant 712, and the surface of coolant 712 is below the top opening of inner container 710. Coolant that has warmed to a gas phase occupies the spaces above coolant 706 and 712. As such, during the spectrum gathering process, optical probe 716 is positioned in the gaseous phase of the coolant.

Preferably, when a diamond is the object being inspected, the diamond is placed, table-down, on the bottom of inner container 710, and fully immersed within and in direct contact with the liquid-phase coolant 712. For photoluminescence spectroscopic analysis, the diamond is position table-up. In practice, the space in inner container 710, above liquid-phase coolant 706, is filled with the gaseous phase of coolant 706. As such, the light-emitting/light-receiving end of probe 716 is positioned within this gaseous phase during the inspecting process.

It has been found that the two-stage cooling apparatus 702 and method embodiments of the present invention essentially eliminates gas-bubbles from around the object being inspected. In FIG. 5, it can be seen that while gas bubbles 718 may be present in the coolant 706 of outer container 704, the cooling effect of coolant 706 on inner container 710 and on coolant 712, is to slow substantially the evaporation rate of coolant 712. As a result, gas bubbles are essentially eliminated within coolant 712, and light passes without interruption within the inner container 710. Further, object 714 can be tested for a much longer time without concern that coolant 712 quickly evaporated and object 714 will become frosted, as compared with the embodiments of FIGS. a, 2A and 2B.

For example, when liquid nitrogen is used as the liquid phase coolant, and a foam cup is used as the outer container 704, the outer surface of the foam cup is directly exposed to room temperature air. The result is a relatively large amount of heat exchange between the room temperature air and the liquid nitrogen in the foam cup (first cooling stage). The liquid nitrogen in the first stage evaporates relatively quickly. However, liquid nitrogen in the inner container (second cooling stage) is surrounded by the liquid nitrogen of the first cooling stage. The liquid nitrogen of the first cooling stage always maintains a temperature of minus 193° C. As a result, the liquid nitrogen in the second cooling stage evaporates very slowly.

The inner container can have a half-ball or hemispherical shape, and the outer container can be cylindrical in shape. The inner container may be supported by appropriate structure such as a disc or legs. The inner container may have a diameter of approximately 40 mm, and a thickness of up to 1 mm. The inner container may also be constructed of Indium or stainless steel.

The two-stage cooling apparatus 702 of the present invention provides a substantially simplified cooling structure, at lower cost, and higher performance, when compared with the embodiments of FIGS. 1, 2A and 2B, and other cooling arrangements.

Figure 6:
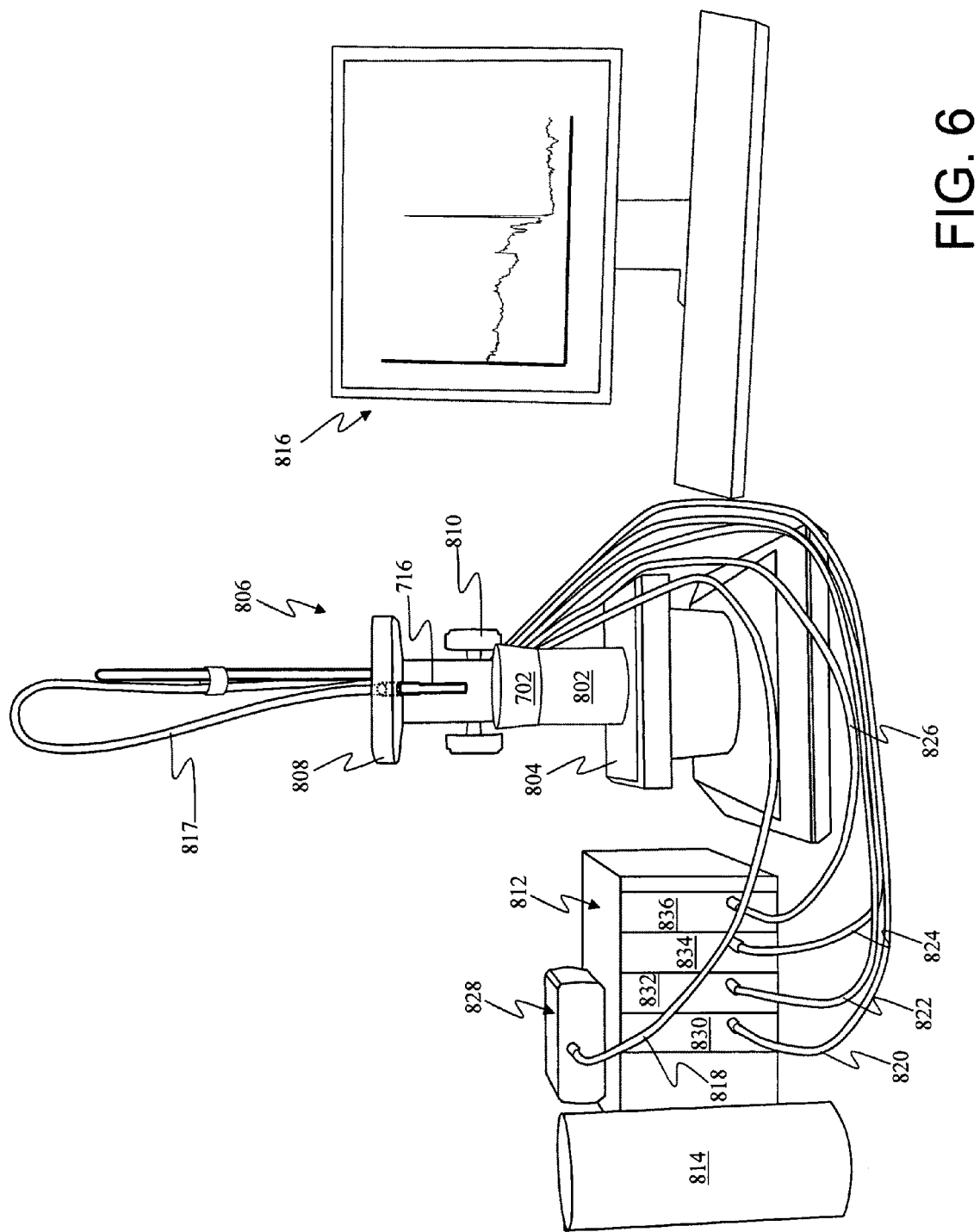
FIG. 6 is a simplified illustration of a system employing an embodiment of a cooling apparatus according to a two-stage cooling embodiment of the invention.

FIG. 6 is a simplified illustration of a preferred system configuration employing the two-stage cooling embodiment of the invention. The two-stage cooling apparatus, 702, of FIG. 5, is shown positioned on a support pedestal 802. Support pedestal 802 is positioned on stage 804 of a microscope 806, such as a gem microscope. Support pedestal 802 may be a block of metal, such as copper, or may be any other structure that is capable of stably supporting two-stage cooling apparatus 702 on the stage of microscope 806. Optical probe 716 is shown supported on the eye piece mount 808 of microscope 806, so that stage positioning knobs 810 may be used to move optical probe 716 into position in inner container 710, not shown, as described earlier. Optical probe 716 may be an optical probe such as those manufactured by Avantes, BV, of Eerbeek, Netherlands. Preferably, optical probe 716 is designed to have a probe head that can project light onto a sample for exciting luminescence, and to collect light from the sample after possible absorption. In use, the collected light is directed to a spectrometer 812. Preferably the spectrometer 812 employs several independent spectrometers in order to increase spectral resolution, although a single spectrometer may be used. Also shown in FIG. 6 are a container 814 of liquid-phase coolant, and a computer display 816 that is used to display the spectrum obtained.

In FIG. 6, a preferred optical cable assembly is shown. The optical cable assembly includes optical cables 817, 818, 820, 822, 824 and 826, having optical fibers that provide optical paths to and from optical probe 716, light source 828, and spectrometers 830, 832, 834, and 836. In a preferred configuration, a bundle of individual optical fibers extend into optical probe 716 to the head of optical probe 716. Several of the fibers are designed to couple light from light source 828 to the head of optical probe 716. Others of the fibers selectively absorb light and direct such selectively absorbed light to corresponding spectrometers. Optical cable 817 routes this full bundle of fibers to a point, not shown, where the fibers are separated out into sub-bundles: one bundle of light source fibers, carried by optical cable 818; one bundle of a first selective absorption fiber, carried by optical cable 820; a second bundle of a second selective absorption fiber, carried by optical cable 822; a third bundle of a third selective absorption fiber, carried by optical cable 824; and a fourth bundle of selective absorption fiber, carried by optical cable 826. Optical cables 820, 822, 824, and 826 then connect to the multiple independent spectrometers 830, 832, 834, and 836, respectively.

In the configuration of FIG. 6, light source 828 is preferably a tungsten halogen light source model AVALight-Hal-S, manufactured by Avantes BV of RB Eerbeek, Netherlands. Each spectrometer includes a slit, preferably of about 10 μm. While such a slit size decreases the amount of light that is passed along to the spectrometers, such slit size permits an increased spectral resolution to be obtained, as compared to using larger slit sizes.

As mentioned above, spectral analysis of light collected by optical probe 716 is preferably performed using a multi-channel spectrometer, for example by using up to four independent spectrometers 830, 832, 834, and 836. Use of a multi-channel spectrometer increases the spectral resolution that may be obtained. In a preferred embodiment, of FIG. 6, spectrometers 830, 832, 834, and 836 are selected to handle spectral signals in the ranges of 193.0-467.7 nm, 449.4-689.0 nm, 675.7-879.4 nm, and 864.2-1039.0 nm, respectively. Suitable spectrometers are available from Avantes BV of RB Eerbeek, Netherlands. In this embodiment, optical cables 820, 822, 824 and 826, may have each have a fiber that selectively absorbs, and thereby passes light most efficiently in the range of 193.0-467.7 nm, 449.4-689.0 nm, 675.7-879.4 nm, and 864.2-1039.0 nm, respectively, to the spectrometers. Thus, it can be appreciated that in a preferred embodiment, spectrometers and subgroups (or sub-bundles) of selective absorption fibers are selected to operate upon a plurality of overlapping ranges from approximately 190 nm to approximately 1050 nm. In other words, each optical cable/spectrometer combination represents a different channel, for example: Channel 1: 193.0-467.7 nm; Channel 2: 449.4-689.0 nm; Channel 3: 675.7-879.4 nm; and Channel 4: 864.2-1039.0 nm. An optical cable/probe assembly of the type described above has been designed and manufactured by Avantes BV of RB Eerbeek, Netherlands, and utilizes 3 optical fibers, each having a 400 µm diameter, and each of which goes to a corresponding spectrometer, and a bundle of 24 optical fibers, each having a 200 µm diameter and connected to the light source for providing illumination.

Compared to the embodiments of the spectral analysis system of FIG. 4, each channel of the preferred embodiment of FIG. 6 covers a much smaller (about ¼) wavelength range, but with the same or similar amount of data points. As a result, the spectral resolution is about 4 times better. Further, the decreased slit size before the spectrometer is important in achieving higher spectral resolution. However, with a decreased slit size, the light reaches the spectrometer is much weaker. For that reason, an integrating sphere, such as is used in the systems of FIG. 4, may not operate satisfactorily. Instead, the optical cable/probe assembly of the type described in connection with FIGS. 5 and 6 above is utilized to overcome this problem by providing a spectrum of high signal to noise ratio. The probe configuration permits the probe head to be positioned very close to the sample so that comparatively more light can be collected. This, in combination with a smaller slit size, helps to increase the ratio of signal to noise of data collected.

Figure 7:
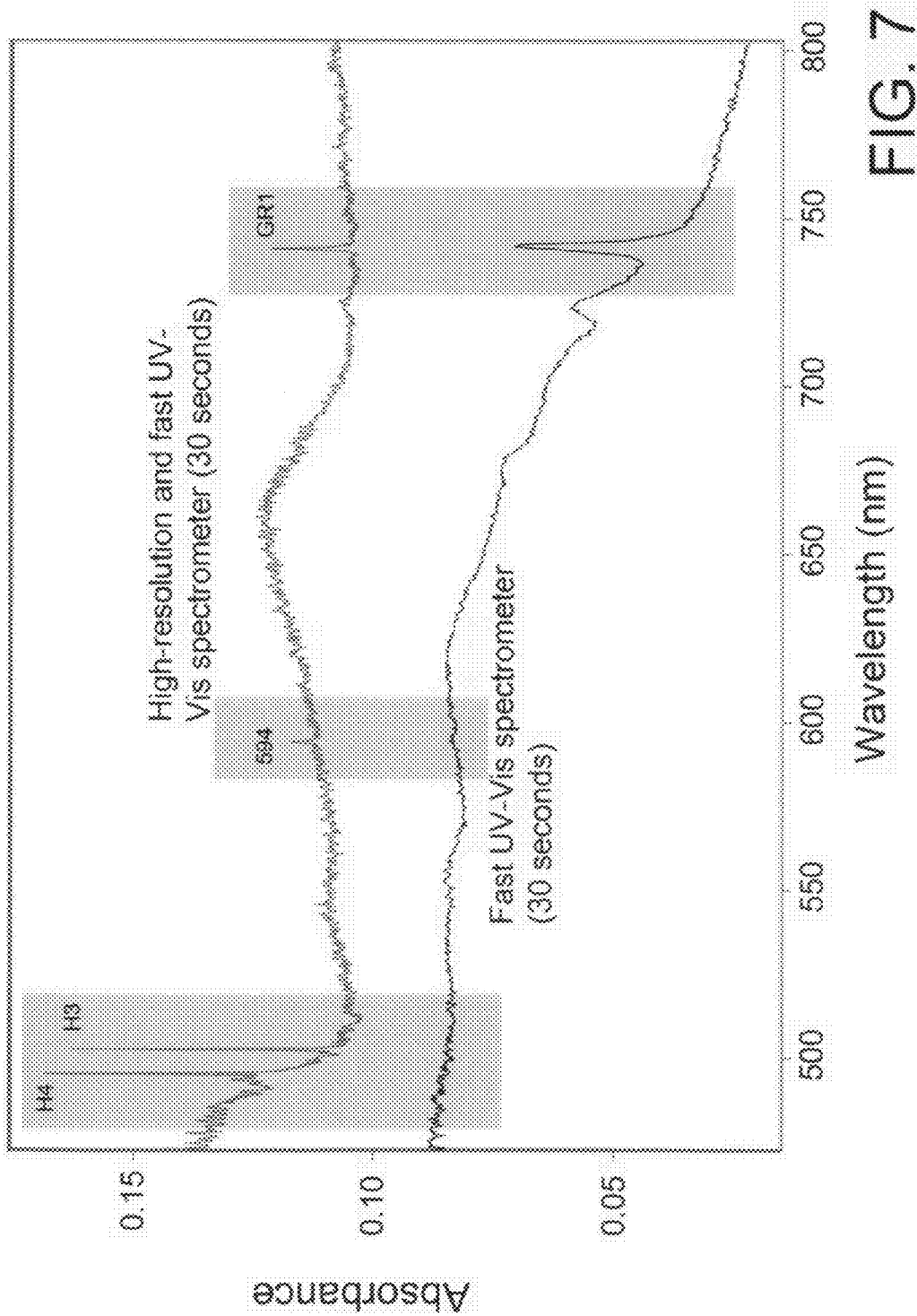
FIG. 7 is a comparative plot of spectral results from inspection of a 4.02 carat, very light blue natural diamond using the two-stage cooling, multiple-channel spectrometer embodiment of the invention compared with results using the cooling apparatus and system of FIG. 4.

FIG. 7 provides a comparative plot of spectral results from inspection of a 4.02 carat, very light blue natural diamond using the two-stage cooling embodiment of the invention versus using the cooling apparatus of FIG. 1, 2A or 2B. As can be seen from the figure, the two-stage cooling embodiments and higher resolution spectrometers permit the acquisition of the spectrum of interest with a substantially higher sensitivity and signal to noise ratio than the other embodiments. In this comparison, absorptions related to defects H4, H3 and 594 nm in diamonds are clearly present in the spectrum obtained using the two-stage cooling and higher resolution spectrometers, while absent in the spectrum obtained using the cooling apparatus of FIG. 1, 2A or 2B. Further, the GR1 signal is substantially more distinct in the spectrum from the two-stage cooling embodiment.

Figure 8:
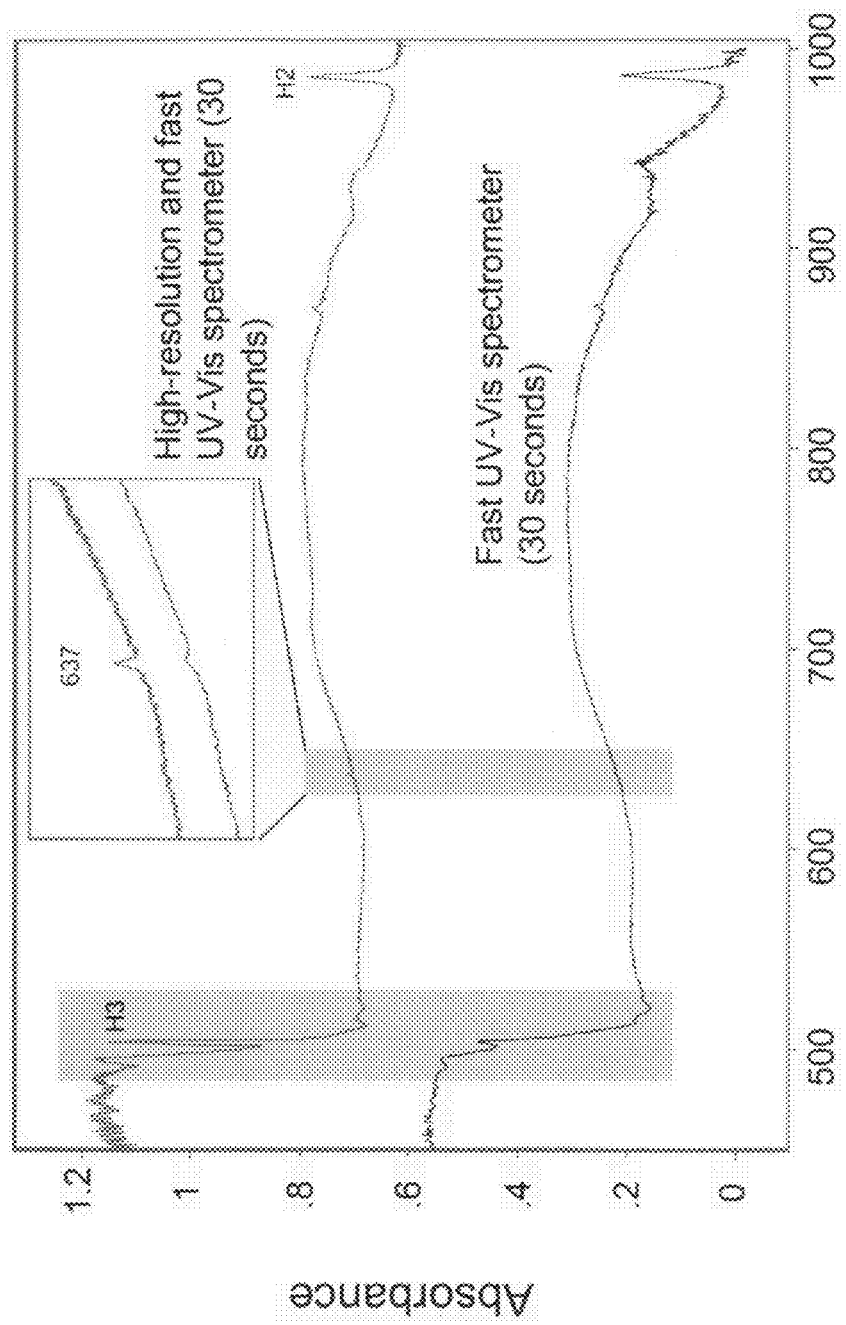
FIG. 8 is a comparative plot of spectral results from inspection of a high pressure, high temperature treated 0.47 carat, fancy vivid green-yellow diamond using the two-stage cooling, multiple-channel spectrometer embodiment of the invention compared with results using the cooling apparatus and system of FIG. 4.

FIG. 8 is a comparative plot of spectral results from inspection of a high pressure, high temperature treated 0.47 carat, fancy vivid green-yellow diamond using the two-stage cooling embodiment of the invention versus using the cooling apparatus of FIG. 1, 2A or 2B. As can be seen from the figure, the two-stage cooling embodiments permit the acquisition of the spectrum of interest with a substantially higher sensitivity and signal to noise ratio than the other embodiments. For example, in FIG. 8, an absorption peak around 637 nm is shown for the two-stage cooling embodiment (top) and the embodiment of FIG. 1, 2A or 2B (bottom). In spectrum obtained using the two-stage cooling embodiment, the 637 nm peak is clearly present, while such component is more obscure in the spectrum from the embodiment of FIG. 1, 2A or 2B. Also, presence of an absorption from the H3 defect is unmistakable in the spectrum from the two-stage cooling embodiment.

Figure 9:
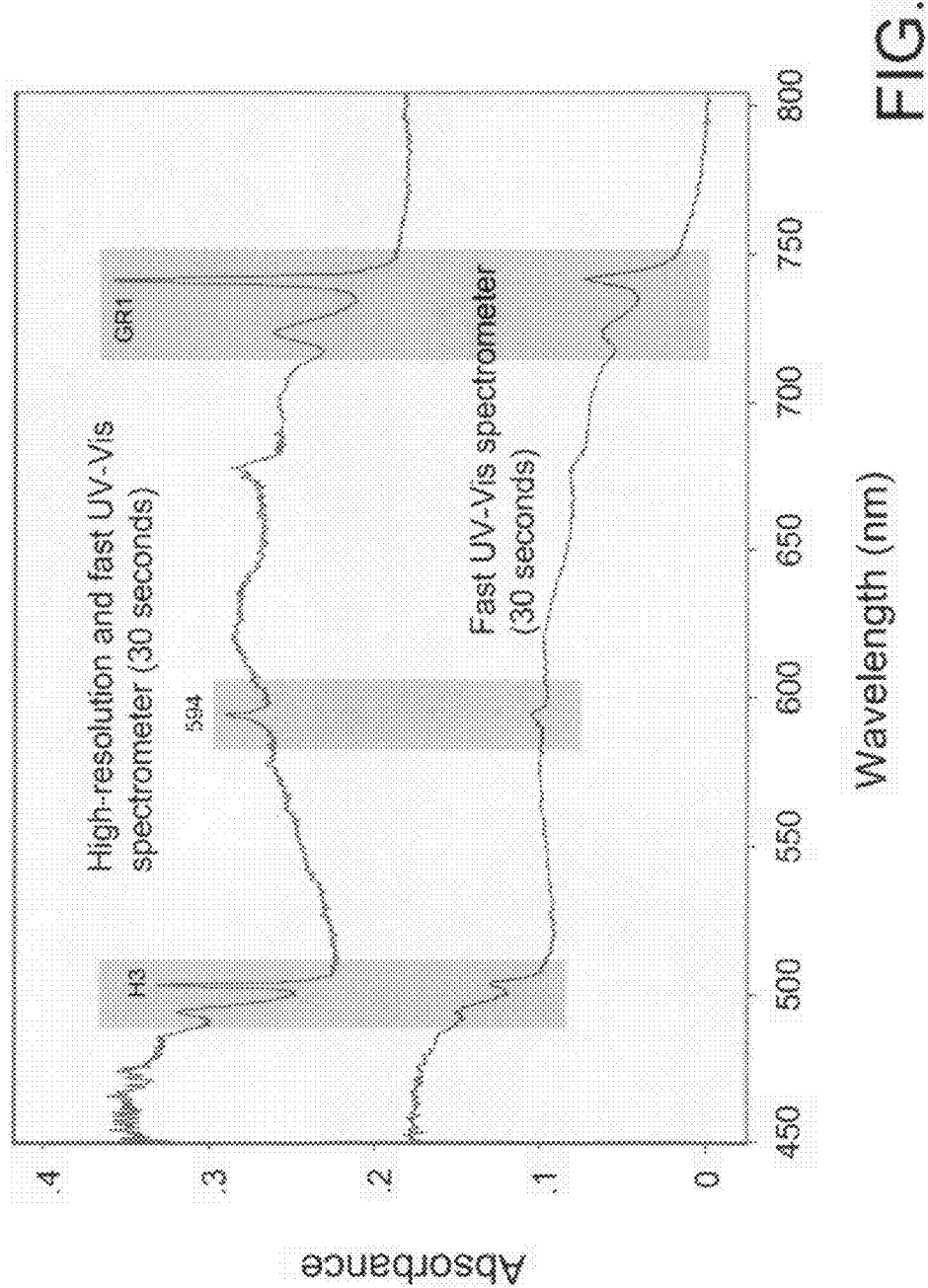
FIG. 9 is a comparative plot of spectral results from inspection of a 1.51 carat, fancy yellowish green diamond, using the two-stage cooling, multiple-channel spectrometer embodiment of the invention compared with results using the cooling apparatus and system of FIG. 4.

FIG. 9 provides a comparative plot of spectral results from inspection of a 1.51 carat, fancy yellowish green diamond, using the two-stage cooling embodiment of the invention versus using the cooling apparatus of FIG. 1, 2A or 2B. As can be seen from the figure, the two-stage cooling embodiments permit the acquisition of the spectrum of interest with a substantially higher sensitivity and signal to noise ratio than the other embodiments. From this comparison of obtained spectrums, it can be seen that the absorption signal levels corresponding to the defects H3, 594 nm and GR1 are significantly greater in magnitude using the two-stage cooling embodiment.

The present invention has been described above with reference to several different embodiments. However, those skilled in the art will recognize that changes and modifications may be made in the above described embodiments without departing from the scope and spirit of the invention. Furthermore, while the present invention has been described in connection with a specific processing flow, those skilled in the art will recognize that a large amount of variation in configuring the processing tasks and in sequencing the processing tasks may be directed to accomplishing substantially the same functions as are described herein. These and other changes and modifications which are obvious to those skilled in the art in view of what has been described herein are intended to be included within the scope of the present invention.

What is claimed is:

1. A cooling apparatus for cooling an object to be inspected comprising:
   an outer container having walls, wherein the outer container is configured to contain a coolant within a space enclosed by the outer container walls;
   an inner container having walls, wherein the inner container is configured to contain a coolant in liquid form within a space enclosed by the inner container walls and shaped to support the object to be inspected within the coolant, and further wherein the inner container is supported in the outer container; and
   a coolant positioned in the outer container to a first level to partially fill the space enclosed by the outer container walls, and positioned in the inner container to a second level to partially fill the space enclosed by the inner container.

2. The cooling apparatus of claim 1, wherein the inner container walls define a hemispherical space and have a circular perimeter.

3. The cooling apparatus of claim 1, wherein the inner container comprises TEFLON® or SPECTRALON®, Aluminum, Indium, or stainless steel.

4. The cooling apparatus of claim 1, wherein the outer container is formed of a thermally insulating material.

5. The cooling apparatus of claim 1, wherein the outer container walls define a cylindrical space and have a circular perimeter.

6. A cooling apparatus for cooling an object comprising:
   a first insulating container having an open end defined by a first perimeter;

a second container positioned within the first container and having an open end defined by a second perimeter; and wherein a space between the second container and walls of the first container is filled with a coolant in a liquid state, and a space within the second container is filled with the coolant, and the object is positioned within the coolant filled space of the second container.

7. The cooling apparatus of claim 6, wherein walls of the second container have an interior hemispherical shape and the perimeter of the second container has a circular shape.

8. The cooling apparatus of claim 6, wherein the perimeter of the first container has a square shape.

9. The cooling apparatus of claim 6, wherein the second container comprises TEFLON® or SPECTRALON®, Aluminum, Indium, or stainless steel.

10. The cooling apparatus of claim 6, further including a disc-shaped support member positioned to support the second container on a bottom of the first container.

11. The cooling apparatus of claim 6, wherein the open end of the second container is configured to permit an optical probe to be positioned within a space within the second container but outside of the coolant filled space.

12. The cooling apparatus of claim 6, wherein the coolant is liquid nitrogen.

* * * * *